(12) United States Patent
Donohue et al.

(10) Patent No.: US 11,371,956 B2
(45) Date of Patent: Jun. 28, 2022

(54) METHODS FOR STABILIZING PALLADIUM FILMS

(71) Applicant: Materion Corporation, Mayfield Heights, OH (US)

(72) Inventors: Lee A. Donohue, Windsor, CT (US); Russell A. Stroud, Simsbury, CT (US); Jerome Farquharson, West Hartford, CT (US); Ian S. Tribick, Groton, MA (US)

(73) Assignee: MATERION CORPORATION, Mayfield Heights, OH (US)

( * ) Notice: Subject to any disclaimer, the term of this patent is extended or adjusted under 35 U.S.C. 154(b) by 0 days.

(21) Appl. No.: 16/007,650

(22) Filed: Jun. 13, 2018

(65) Prior Publication Data

US 2018/0356362 A1    Dec. 13, 2018

Related U.S. Application Data

(60) Provisional application No. 62/518,989, filed on Jun. 13, 2017.

(51) Int. Cl.
  *C23C 26/00*  (2006.01)
  *C23C 14/14*  (2006.01)
  (Continued)

(52) U.S. Cl.
  CPC ......... *G01N 27/3272* (2013.01); *C12Q 1/003* (2013.01); *C12Q 1/006* (2013.01);
  (Continued)

(58) Field of Classification Search
  CPC ....... C23C 14/14; C23C 14/20; C23C 14/205; C23C 14/5826; C23C 26/00; C23C 14/582; G01N 27/3271; G01N 27/3272; G01N 27/3275; G01N 27/3277; C12Q 1/001–006
  (Continued)

(56) References Cited

U.S. PATENT DOCUMENTS 4,536,274 A * 8/1985 Papadakis .......... A61B 5/14539
                                                    204/415
5,573,733 A * 11/1996 Salama .................. B01J 19/088
                                                    204/176
(Continued)

FOREIGN PATENT DOCUMENTS

WO    WO 2011/106057 A2    9/2011
WO    WO 2013/059534 A1    4/2013

OTHER PUBLICATIONS

Robert C. Weast, PhD, editor; CRC Handbook of Chemistry and Physics, 56th edition; CRC press, 18901 Cranwood Parkway; Cleveland, OH 44128; 1975 (no month) excerpt p. F-206.*
(Continued)

*Primary Examiner* — Dah-Wei D. Yuan
*Assistant Examiner* — Nga Leung V Law
(74) *Attorney, Agent, or Firm* — Tucker Ellis LLP

(57) ABSTRACT

The present disclosure relates to methods of creating a biosensor. A palladium film is deposited onto a surface of a substrate. The palladium film is then treated with an air plasma to stabilize the palladium and reduce or eliminate its catalytic activity. The biosensor is created from the treated palladium film and the substrate.

20 Claims, 3 Drawing Sheets

(51) Int. Cl.
*C23C 14/58* (2006.01)
*G01N 27/327* (2006.01)
*C12Q 1/00* (2006.01)

(52) U.S. Cl.
CPC .......... *C23C 14/14* (2013.01); *C23C 14/5826* (2013.01); *C23C 26/00* (2013.01); *G01N 27/3277* (2013.01)

(58) Field of Classification Search
USPC ................ 427/2.11, 534, 535, 537, 539, 125
See application file for complete search history.

(56) References Cited

U.S. PATENT DOCUMENTS

| | | | | |
|---|---|---|---|---|
| 6,001,429 A | * | 12/1999 | Martin | .................. C23C 16/402 427/237 |
| 2004/0070006 A1 | * | 4/2004 | Monty | ................. G01N 27/127 257/200 |
| 2009/0038939 A1 | * | 2/2009 | Popovich | ............... C12Q 1/005 204/401 |
| 2013/0056241 A1 | * | 3/2013 | Gao | .......................... B03C 3/41 174/126.2 |
| 2013/0136654 A1 | * | 5/2013 | Ryu | .......................... A61L 2/14 422/29 |
| 2014/0342122 A1 | * | 11/2014 | Inglis | .................. C23C 16/4586 428/141 |
| 2015/0230737 A1 | * | 8/2015 | Heller | .................... B82Y 30/00 600/345 |
| 2015/0276651 A1 | * | 10/2015 | Petisce | ...................... C23F 1/44 204/403.1 |
| 2016/0030622 A1 | * | 2/2016 | Li | .............................. A61L 9/22 422/122 |
| 2017/0275499 A1 | * | 9/2017 | Hahnel | ................... B32B 37/10 |
| 2019/0376960 A1 | * | 12/2019 | Ashford, II | ............. C23C 14/34 |

OTHER PUBLICATIONS

International Search Report dated Aug. 21, 2018 from PCT/US2018/037371.

* cited by examiner

METHODS FOR STABILIZING PALLADIUM FILMS

CROSS-REFERENCE TO RELATED APPLICATIONS

This application claims priority to U.S. Provisional Patent Application Ser. No. 62/518,989, the entirety of which is fully incorporated by reference herein.

BACKGROUND

The present disclosure relates to methods for creating a biosensor. In particular, the methods are directed to creating a biosensor with palladium electrodes that have stabilized electrical and surface energy properties when exposed to an ambient environment, and will be described with particular reference thereto. However, it is to be appreciated that the present disclosure is also amenable to other like applications.

Biosensors are used for several applications, such as measuring the amount of an analyte (e.g., glucose) in a biological fluid (e.g., blood). Blood glucose monitoring is a valuable tool in the management of diabetes. Diabetes is a disease in which the body is unable to control tightly the level of blood glucose, which is the most important and primary fuel of the body. This is due to either the pancreas not producing enough insulin, or to the cells of the body not responding properly to the insulin produced. Patients with diabetes are encouraged to monitor their glucose levels to prevent hyperglycemia, as well as other long-term complications such as heart disease, stroke, kidney failure, foot ulcers, and eye damage. A glucose biosensor is an analytical device for detecting the analyte, glucose, in the blood. Although glucose biosensors have been devised based on potentiometry, amperometry, and colorimetry, to date most commercially available biosensors are amperometric biosensors. These biosensors use a redox enzyme (e.g., glutathione peroxidases (GPX), nitric oxide synthase (eNOS, iNOS, and nNOS), peroxiredoxins, super oxide dismutases (SOD), thioredoxins (Trx), and the like), as the biological component responsible for the selective recognition of the analyte of interest (e.g., glucose).

A biosensor of this type is a relatively small strip of laminated plastic that can be exposed to a biological sample such as blood. An important feature of the biosensor is that it is disposable and only used one time. The strip acts as a substrate for a reaction chamber and two electrodes, a reference electrode and a working electrode, which are connected to the reaction chamber. The glucose biosensor contains a reagent layer that is attached to the working electrode. The reagent layer includes the selective recognition component (i.e., the redox enzyme) as well as electron mediators or other substances, which can help facilitate the reaction or help stabilize the reagent layer itself. The biological fluid sample is introduced into the reaction chamber of the glucose biosensor and the biosensor is connected to a measuring device such as a meter for analysis using the biosensor's electrodes. The analyte (glucose) in the sample undergoes a reduction/oxidation reaction at the working electrode (where the redox enzyme is located) while the measuring device applies a biasing potential signal through the electrodes of the biosensor. The redox reaction produces an output signal in response to the biasing potential signal. The output signal usually is an electronic signal, such as potential or current, which is measured and correlated with the concentration of the analyte in the biological fluid sample.

In building the biosensor, a palladium film is deposited onto a substrate to act as an electrode. Palladium is known to be a highly conductive material, which is desirable for an electrode. This deposition is usually performed under vacuum conditions.

While palladium is a desirable material to use in forming an electrode, there are some complications with its use. In particular, palladium is somewhat catalytic when exposed to ambient conditions (e.g., air containing 77% $N_2$/21% $O_2$ at standard temperature and pressure, exposure to sunlight, etc.). This is undesirable because it means the electrical performance characteristics of the biosensor will change depending on the amount of time the biosensor has been exposed to ambient conditions. As a result, the electrochemical energy and the surface energy of freshly sputtered palladium films can vary between biosensors. The output signal provided by the measuring device could thus change depending on the biosensor, not only on the concentration of the analyte as is most preferred.

Accordingly, it would be desirable to develop new methods of creating a biosensor with a palladium film which have an electrical performance that is stable and predictable over time. This permits large batches of biosensors to be made at a time and stored, and then used without having to worry that the storage time will affect the reliability of the reading provided by the biosensor. Such biosensors can be used in many different applications.

BRIEF DESCRIPTION

The present disclosure relates to methods of creating a biosensor. A palladium film is formed on a surface of a substrate. The palladium film is then treated to stabilize the film such that any catalytic activity of the film is reduced or eliminated, or in other words so that its electrical and surface energy properties are more consistent over time. It is contemplated that this can be done by completely reacting the palladium film so that it can no longer catalyze any reaction. The palladium film can be treated by exposure to an air plasma (i.e. containing about 78% $N_2$ and about 21% $O_2$).

In some embodiments, the palladium film is subsequently coated with 2-mercaptoethane sulfonate (MESA) after the air plasma treatment. This coating can reduce the presence of oxide species on the palladium film.

In other embodiments, a reaction chamber is formed in the substrate. The reaction chamber contacts the treated palladium film.

In some embodiments, a reagent layer is formed on the treated palladium film to form a working electrode. In other embodiments, the treated palladium film operates as a reference electrode. A second electrode is formed on the substrate. A reagent layer is placed on the second electrode to form a working electrode.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
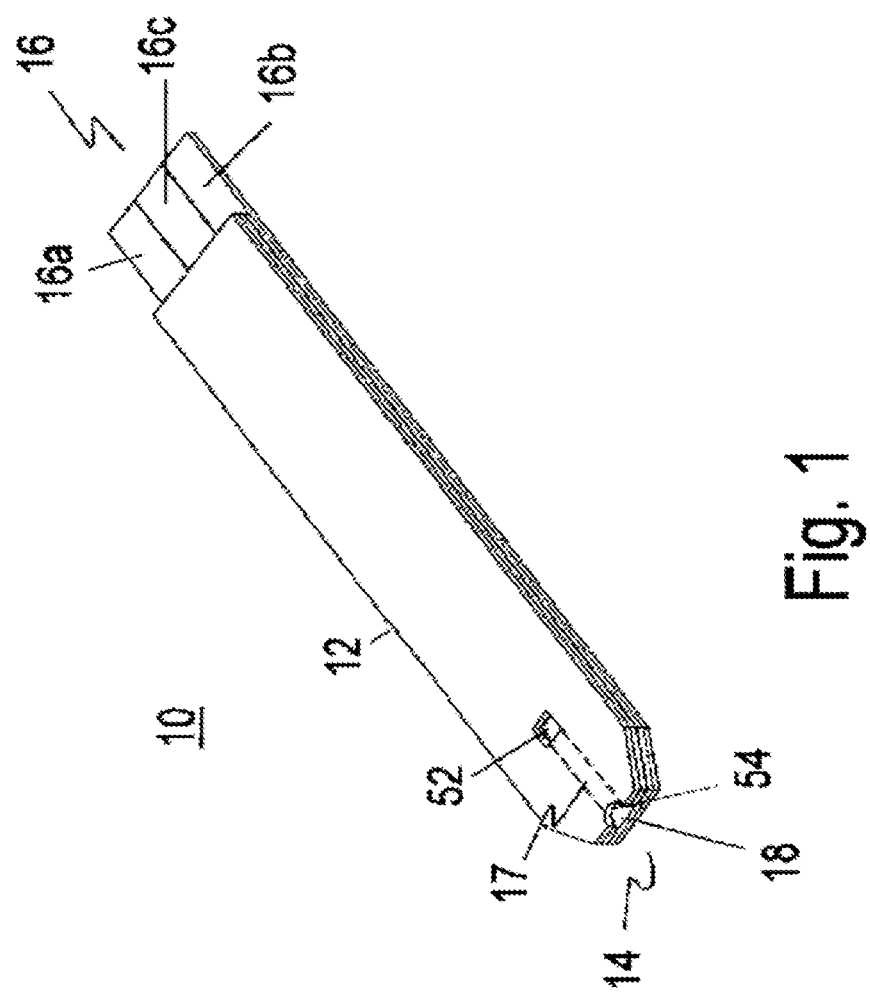
FIG. 1 is a perspective view of an exemplary biosensor of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

The term "exposure to ambient conditions" and variants thereof refers to exposing the biosensor to air containing 78 vol % $N_2$/21 vol % $O_2$ at standard temperature and pressure and under sunlight.

The term "reagent" and variants thereof refers to a composition that may include multiple ingredients. For example, the reagent is sometimes used herein to describe a composition containing a redox enzyme, electron mediators, and additional substances/compounds. A reagent can be liquid or solid.

It has been found that, upon exposure to ambient conditions, the performance characteristics of a palladium film are modified. The electrical characteristics change and the surface energy decreases (manifested by a water contact angle increase). This modification stabilizes after approximately 60-90 days. It is believed that during this time, a thin passive film (1-2 monolayers thick) is formed on the palladium film. The thickness and the chemistry of the passive film significantly impacts the characteristics of the biosensor. The palladium film can be treated to rapidly accelerate these changes and obtain stabilized properties without this extended stabilization time. This provides practical methods for producing a biosensor with an electrical performance that is stable and predictable (i.e., does not change significantly over time).

FIG. 1 is a perspective view of a biosensor 10. The biosensor 10 has a body 12, a fluid sampling end 14, an electrical contact end 16, and a vent opening 52. A notch 54 is disposed at the fluid sampling end 14 to facilitate loading of the fluid sample into the sample chamber 17. The fluid sampling end 14 includes a sample chamber 17 between a sample inlet 18 and the vent opening 52. The electrical contact end 16 has three discrete conductive contacts 16a, 16b, and 16c.

Figure 2:
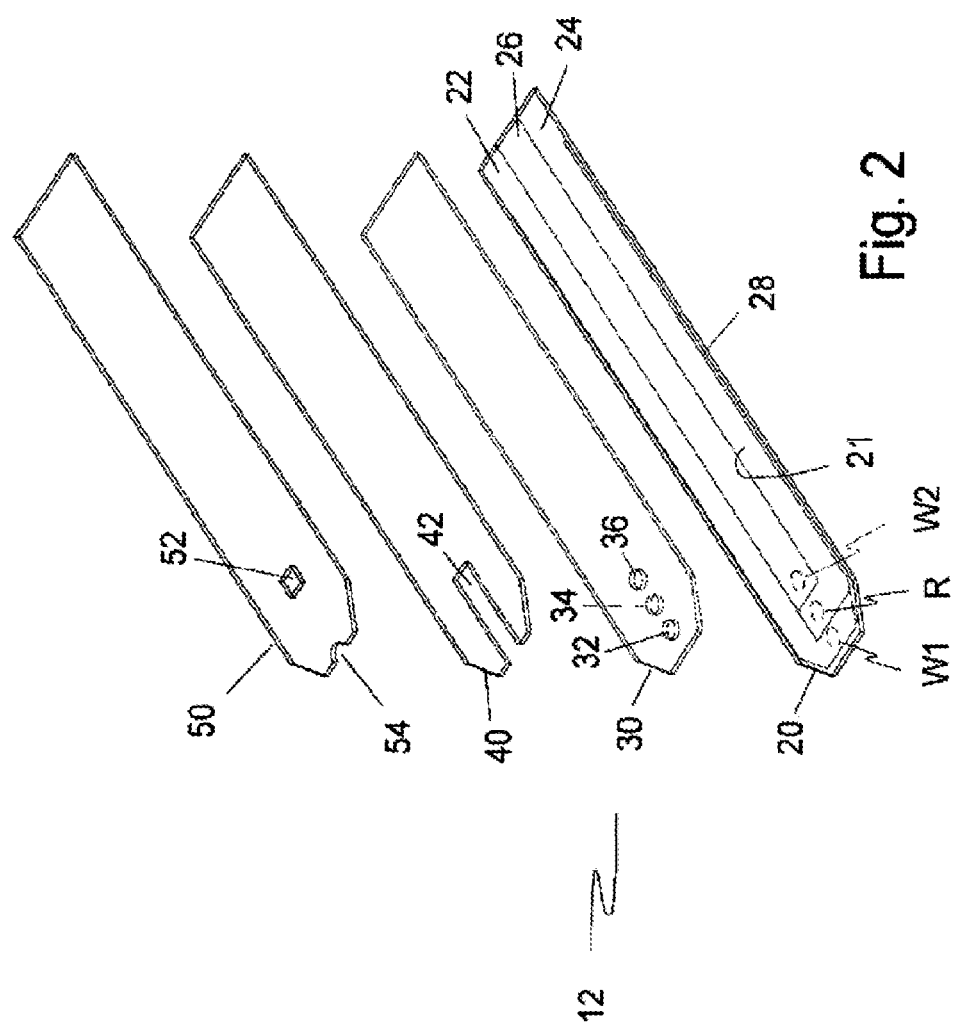
FIG. 2 is an exploded view of the biosensor of FIG. 1.

FIG. 2 is an exploded view of the biosensor 10. The body 12 is composed of a substrate 20, an optional reagent holding layer 30, a channel forming layer 40, and a cover 50. The layers of the body 12 are generally made of plastics such as polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

The substrate 20 has a palladium film 21 on which are delineated three electrodes 22, 24 and 26. The electrodes 22, 24, 26 may be formed by scribing or scoring the palladium film 21, or by silk-screening electrodes 22, 24, 26 onto substrate 20. Scribing or scoring of the palladium film 21 may be done by mechanically scribing the palladium film 21 sufficiently to create the three independent electrodes 22, 24, 26. The preferred scribing or scoring method of the present invention is done by using a carbon dioxide laser, a YAG laser or an excimer laser. Alternatively, the palladium film is patterned as it is laid down, such that the palladium film forms one electrode. As illustrated here, three different films would be deposited to form the three electrodes 22, 24, 26.

The reagent holding layer 30 can be used when liquid reagents are desired to be used. The reagent holding layer 30 has three reagent holding openings 32, 34 and 36. The reagent holding opening 32 exposes a portion of the electrode 22, the reagent holding opening 34 exposes a portion of the electrode 24, and the reagent holding opening 36 exposes a portion of the electrode 26 creating reagent holding wells. This layer 30 is used to hold a sufficient quantity of chemical reagents in liquid form and to promote capillary action through the sample chamber of the sensor. The reagent holding layer 30 may be made from a plastic sheet and may be coated with a pressure sensitive adhesive, a photopolymer, ultrasonically-bonded to substrate 20, or silk-screened onto the substrate 20.

Usually, the channel forming layer 40 has a U-shaped cutout 42 located at the fluid sampling end 14. The length of the cutout 42 is such that when the channel forming layer 40 is laminated to reagent holding layer 30, electrode areas W and R are within the space defined by the cutout 42. The length, width and thickness of the U-shaped cutout 42 define the capillary channel volume.

The three reagent holding openings 32, 34, 36 define electrode areas W1, W2, and R, respectively, and hold chemical reagents forming two working electrodes and one reference electrode. Generally, the electrode areas are loaded with the reagent mixtures. The reagent mixtures for the working electrode areas 32, 34, 36 are a mixture of enzymes and redox mediators with optional polymers, surfactants, and buffers. A reference reagent matrix may be loaded in electrode area R that is similar to the reagent mixture of the working electrodes. It is contemplated that W1 and W2 use different enzymes/mediators, which can be used to check each other. Embodiments are also contemplated that have only one working electrode, which may be simpler to manufacture.

Alternatively, the chemical reagents can be used to form a reagent layer in the form of a dried solid film on the electrode areas W1, W2, R. In these embodiments, the reagent holding layer 30 is not needed.

Typically, electrode area R must be loaded with a redox reagent or mediator to make the reference electrode function. The reference reagent mixture preferably contains either oxidized or a mixture of an oxidized and reduced form of redox mediators, at least one binder, a surfactant and an antioxidant (if a reduced form of redox mediator is used) and a bulking agent. In the alternative, the reference electrode (electrode area R) could be also loaded with a Ag/AgCl layer (e.g. by applying Ag/AgCl ink or by sputter-coating a Ag or Ag/AgCl layer) or other reference electrode materials that do not require a redox mediator to function properly.

The size of the reagent holding openings is desirably as small as possible while still being capable of holding sufficient chemical reagent to function properly. As depicted here, the reagent holding openings are round and have a preferred diameter of about 0.03 in. (0.76 mm). The three reagent holding openings 32, 34, 36 are aligned with each other and are spaced about 0.025 in. (0.625 mm) from each other. The circular reagent holding openings are for illustrative purposes only and it should be understood that the shape of the reagent holding openings is not critical.

When a fluid sample is applied to a single strip of the present disclosure, the fluid sample enters the channel through the sampling end aperture and flows over W1, W2 and R and stops at the threshold of the vent opening. Chronoamperometry (i-t curve) can be used to measure the current response of the biosensor. Oxygen concentration ($pO_2$) can be controlled. Once a blood sample enters the strip, a potential of 0.3-0.5 volts is applied across the working electrodes and the reference electrode. The glucose concentration of the blood sample can then be measured.

The above described embodiments are based on amperometric analyses. Those skilled in the art, however, will recognize that a sensor of the present disclosure may also utilize coulometric, potentiometric, voltammetric, and other electrochemical techniques to determine the concentration of an analyte in a sample.

Oxygen plasma (i.e. 100% $O_2$) has previously been used to passivate palladium films, but has resulted in films with different thicknesses and chemical properties compared to naturally formed passivated films (i.e. obtained after 60-90 days of exposure to ambient conditions). This has led to detrimental surface capacitance decreases in sensing devices and performance. In the present disclosure, the palladium film is treated with an air plasma instead of oxygen plasma. Air plasma is based on air, which contains nitrogen and oxygen. The nitrogen is usually present in an amount of about 78% (by volume) and about 21% $O_2$ (by volume). Argon may also be present in air, in an amount of about 1% by volume. Other hydrocarbon species may also be present in the air. The use of air to form the plasma provides greater control over the thickness of the stabilized palladium film. The resulting surface properties of the stabilized palladium film are also more similar to those obtained under ambient conditions after a stabilization period of 60-90 days.

Figure 3:
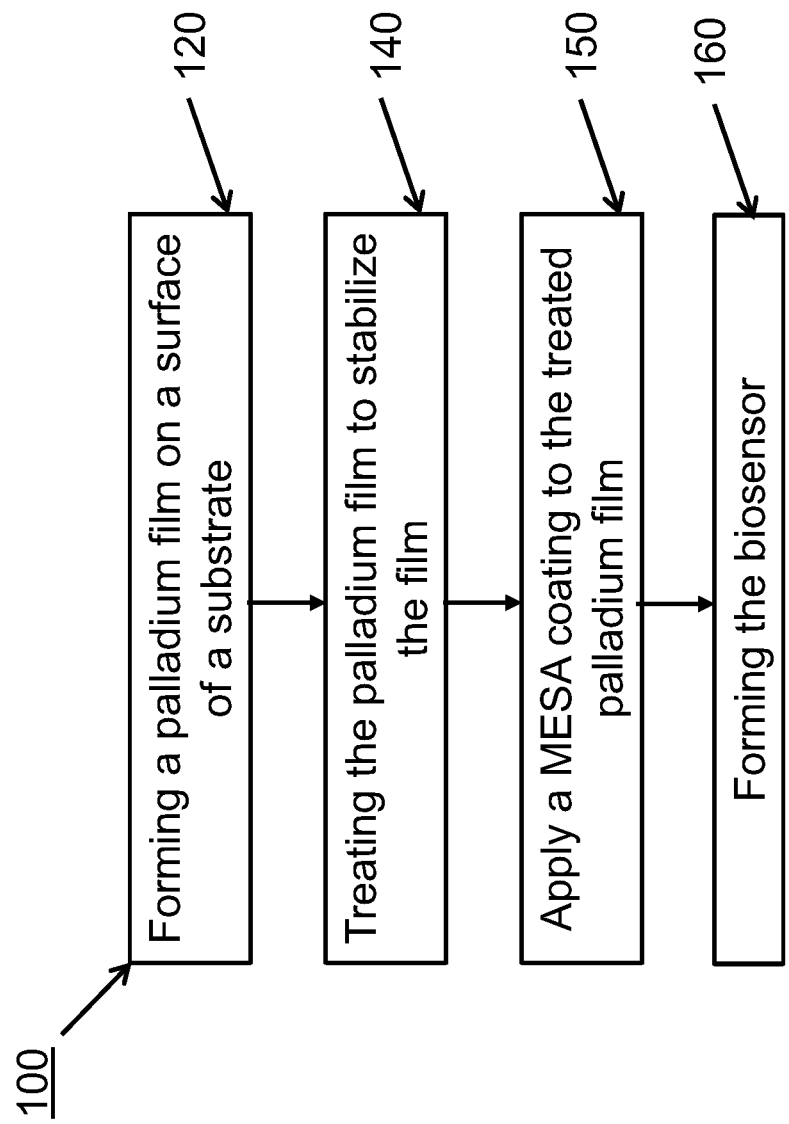
FIG. 3 is a flow chart illustrating an exemplary method of the present disclosure.

FIG. 3 is a flowchart that illustrates an exemplary method 100 of creating a biosensor such that the electrochemical energy and the surface energy of the palladium film are reduced. As a result, the palladium film will not operate as a catalyst. The method 100 includes the steps of: forming a palladium film onto a surface of a substrate (Step 120); treating the palladium film to passivate it (Step 140); and forming the biosensor (Step 160).

At Step 120, a palladium film is formed on a surface of a substrate. For example, the palladium layer is deposited onto the substrate surface by using fast ions to eject particles of palladium from a palladium source due to contact of the palladium source by energetic particles. The palladium film can be formed by sputtering, or by chemical vapor deposition, or by other methods recognized in the art. Prior to coating the substrate, the surface of the substrate can be plasma-treated to clean the surface and to enhance adhesion of the palladium film to the surface. The substrate is usually provided in the form of a web that is fed through a coating chamber at a rate of 1 ft/min to 100 ft/min, including from about 20 ft/min to about 40 ft/min.

At Step 140, the palladium film is treated to reduce or eliminate its catalytic activity. The palladium film is treated with an air plasma.

More particularly, plasma is produced by introducing reactive gas molecules to an electric field. Excitation of the reactive gas molecules results in a partially ionized medium comprising a variety of energetic particles (plasma). These energetic particles then react with the palladium. The reactive gas here is a mixture of about 78 vol % nitrogen ($N_2$) and about 21 vol % oxygen ($O_2$). The plasma treatment is usually performed in a low pressure vacuum environment. An atmospheric plasma gun can be used for this purpose, as can other ion sources such as a wide area low pressure glow discharge source, a high pressure source, or an ion source. The pressure can be from about 10 milliTorr (mTorr) to about 200 mTorr. The air can be provided as compressed air. The distance between the plasma source and the substrate is from 1 inch to about 5 feet, and is typically from 1 inch to about 1 foot.

The plasma treatment can be performed at a power of 1 watt to 20 kilowatts (kW). In particular embodiments, the power is from about 1 kW to about 2 kW. The power supply can be direct current (DC), although pulsed, mid-frequency, and radio frequency (RF) can also be used. The gas used to form the air plasma may be provided at a rate from 1 standard cc/min (sccm) to 5000 sccm. Argon can be used as the working gas, with air as the reactive gas. The working gas can be provided at a rate of 1 sccm to 5000 sccm. The reactive gas can be provided at a rate of 30 sccm to 500 sccm.

The palladium film can be analyzed to determine the electrochemical energy and the surface energy of the treated palladium film. For example, the treated palladium layers can be analyzed based on evaluation of contact angle, surface energy, and/or cyclic voltammetry of each treated palladium film layer. In particular, cyclic voltammetry has been found to be effective in predicting the surface state of the palladium film, and thus its ability to act as a catalyst. Since cyclic voltammetry and contact angle measurements are critical to an optimized palladium layer, it is desirable to select the treatment option which most enhances these features.

If desired, at Step 150, the treated palladium film can be coated with 2-mercaptoethane sulfonate (MESA). This reduces oxide species formation on the surface of the treated palladium film.

At Step 160, the biosensor is formed with the treated palladium film. In this regard, the biosensor may include additional features (e.g. a reaction chamber) that need to be made to the substrate, or other components (such as those depicted in FIG. 2) need to be assembled to form the completed biosensor.

This process for treating the palladium film reduces the storage/aging time that needs to be used to stabilize the properties of the palladium film before using the palladium film in the formation of a biosensor. This reduces manufacturing costs, adding value and increasing production efficiency. It is noted that treatment with oxygen plasma (100% $O_2$) results in a negative impact to device capacitance which does not occur when air plasma treatment is used instead. It is believed that instead of a pure oxide film being formed on the palladium film, a thin complex O—C—H layer is formed when using air plasma. The air plasma treatment could potentially also be used to stabilize the surface properties of other metal coatings.

EXAMPLES

Three different treatments were applied to palladium films. In the "Standard" treatment, the palladium film was not treated with plasma at all, but rather aged via storage for 90+ days. For the "Plasma MESA" treatment, the palladium film was treated with oxygen plasma (100 vol % $O_2$), and then coated with MESA. For the "Plasma" treatment, the palladium film was treated with oxygen plasma (100 vol % $O_2$), and was not coated with MESA. Multiple samples of these three films were tested at 0, 4, 6, and 8 weeks with three different amounts of glucose (50, 250, and 500 milligrams per deciliter (mg/dL)), and the capacitance (nanofarads, or nF) was measured at 30° C.

For the "Plasma MESA" films, there was a decrease in capacitance compared to the "Standard" films. At 250 and 500 mg/dL glucose, the capacitance decreased about 3%. But at 50 mg/dL glucose, the decrease was about 6%.

This decrease in capacitance was even worse for the "Plasma" films that were not treated with MESA. When compared to the "Standard" films at 250 and 500 mg/dL glucose, the capacitance decreased between 6% and 9%. But at 50 mg/dL glucose, the decrease was about 12-16%. The error also increased over time. The use of $O_2$ plasma had a negative effect on the films.

Next, palladium films treated using pure $O_2$ plasma were compared to palladium films treated using compressed air plasma, an "Uncoated Pd" that had no plasma treatment or MESA coating, and a "Coated Pd" that had no plasma treatment but was coated with MESA. Different treatments were applied which varied by web speed, power, voltage, and gas feed rate. These split treatments were compared to palladium films not treated with plasma.

The capacitance of each split was measured using two control solutions, a high solution (350 mg/dL glucose) and a low solution (120 mg/dL glucose), measured at 0 weeks. For each split, the capacitance was lower for the low solution. The splits that were treated with oxygen plasma all had similar capacitances.

Next, multiple samples were tested at five different glucose levels. The samples were tested at 50, 250, and 500 mg/dL glucose. The two control solutions, 120 mg/dL and 350 mg/dL, were also tested.

Next, the capacitance was measured. Compared to the "Standard", "Plasma MESA", and "Plasma" treatments that used $O_2$ plasma, when air plasma was used, even at low glucose concentrations the capacitance response did not drop away, varying by less than 1% between 50 mg/dL and 500 mg/dL. The behavior was very flat and similar to atmospherically aged effects.

Generally, the air-treated splits produced transients similar to the coated Pd splits. The uncoated Pd split had a shallower peak. The oxygen plasma treated splits produced a higher % of errors compared to the other splits.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method of creating a biosensor, comprising:
forming a first electrode used in a biosensor, comprising:
forming a palladium film on a surface of a substrate; and
treating a surface of the palladium film with an air plasma coating process to add a stabilizing film to the surface of the palladium film, resulting in the first electrode of a biosensor comprised of a treated palladium film of palladium film coated with the stabilizing film, wherein the air plasma coating process comprises:
using a flow of gas comprising about 78 vol % nitrogen and about 21 vol % oxygen, at a flow rate of about 2 sccm to about 1000 sccm;
applying a vacuum at a negative pressure of about 10 mTorr to about 200 mTorr;
applying power at about 1 W to about 20 kW; and
wherein the resulting stabilizing film has a contact angle that is substantially equivalent to a palladium film that has been aged in ambient conditions over 60 to 90 days.

2. The method of claim 1, further comprising forming a reaction chamber on the substrate, the reaction chamber contacting the first electrode.

3. The method of claim 1, further comprising forming a reagent layer on the treated palladium film so that the first electrode operates as a working electrode, the reagent layer comprising a selective recognition component for an analyte.

4. The method of claim 1, wherein the first electrode operates as a reference electrode, and further comprising forming a second electrode on the substrate, and placing a reagent layer on the second electrode to form a working electrode, the reagent layer comprising a selective recognition component for an analyte.

5. The method of claim 1, wherein the palladium film is treated with the air plasma at the power of 1 W to 3 kW.

6. The method of claim 1, wherein the palladium film is treated with the air plasma using the gas flow of about 5 sccm to about 20 sccm.

7. The method of claim 1, wherein the substrate is provided in the form of a web, and wherein the palladium film is treated with the air plasma at a web speed of about 1 ft/min to about 100 ft/min.

8. The method of claim 1, wherein the palladium film is treated with the air plasma at the negative pressure of about 10 mTorr to about 20 mTorr.

9. The method of claim 1, wherein a distance between the substrate and a plasma treatment source is about 1 inch to about 5 feet when the palladium film is treated with the air plasma.

10. The method of claim 1, wherein the palladium film is treated with the air plasma at the power of about 1 kilowatt to about 5 kilowatts and using the gas flow of about 30 sccm to about 500 sccm, and the negative pressure of about 10 mTorr to about 20 mTorr.

11. The method of claim 1, wherein the substrate is provided in the form of a web, and wherein the palladium film is treated with the air plasma at the power of about 1 watt to about 10 kilowatts and using at a web speed of about 1 ft/min to about 100 ft/min.

12. The method of claim 1, wherein the palladium film is treated with the air plasma at the power of about 1 watt to about 10 kilowatts and using the negative pressure of about 10 mTorr to about 100 mTorr.

13. The method of claim 1, further comprising coating the treated palladium film with 2-mercaptoethane sulfonate, resulting in a coated, treated palladium film.

14. The method of claim 1, wherein the flow of gas comprising about 78 vol % nitrogen and about 21 vol % oxygen comprises a reactive gas, the air plasma coating process further comprising using a flow a working gas at a flow rate of about 2 sccm to about 1000 sccm, the working gas comprising argon.

15. The method of claim 1, wherein the resulting stabilizing film has a thin complex O-C-H layer.

16. The method of claim 1, wherein the resulting stabilizing film has a capacitance error that is substantially equivalent to a palladium film that has been aged in ambient conditions over 60 to 90 days.

17. The method of claim 1, wherein the contact angle measures a surface energy that is consistent over time.

18. The method of claim 1, wherein the resulting stabilizing film has catalytic activity that is substantially equivalent to a palladium film that has been aged in ambient conditions over 60 to 90 days.

19. The method of claim 1, wherein the resulting stabilizing film has a stable and predictable electrical performance over time.

20. The method of claim 1, wherein the resulting stabilizing film has a surface energy determined by cyclic voltammetry.

* * * * *